(12) United States Patent
Kim et al.

(10) Patent No.: US 10,088,897 B2
(45) Date of Patent: Oct. 2, 2018

(54) METHOD AND ELECTRONIC DEVICE FOR IMPROVING PERFORMANCE OF NON-CONTACT TYPE RECOGNITION FUNCTION

(71) Applicant: Samsung Electronics Co., Ltd., Gyeonggi-do (KR)

(72) Inventors: Kyunghwa Kim, Seoul (KR); Sihak Jang, Gyeonggi-do (KR); Jihong Jeung, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 14/244,841

(22) Filed: Apr. 3, 2014

(65) Prior Publication Data

US 2014/0300535 A1    Oct. 9, 2014

(30) Foreign Application Priority Data

Apr. 3, 2013  (KR) .......................... 10-2013-0036365

(51) Int. Cl.
| | |
|---|---|
| *G06F 3/13* | (2006.01) |
| *G06K 9/00* | (2006.01) |
| *G06F 3/01* | (2006.01) |
| *A61B 3/113* | (2006.01) |

(52) U.S. Cl.
CPC ......... *G06F 3/013* (2013.01); *G06K 9/00597* (2013.01); *A61B 3/113* (2013.01); *G06K 9/00221* (2013.01)

(58) Field of Classification Search
CPC .... G06F 3/011; G06F 17/30793; G06F 3/013; G06K 9/00221; G06K 9/00597; A61B 3/113
See application file for complete search history.

(56) References Cited

U.S. PATENT DOCUMENTS

| | | | |
|---|---|---|---|
| 2005/0225723 A1* | 10/2005 | Pilu ............................... | 351/209 |
| 2010/0125816 A1* | 5/2010 | Bezos ........................... | 715/863 |
| 2014/0058241 A1* | 2/2014 | Apparies ............ | A61B 5/04842 600/383 |
| 2014/0176813 A1* | 6/2014 | Conness et al. .............. | 348/738 |

* cited by examiner

*Primary Examiner* — Michael Faragalla
*Assistant Examiner* — Chayce Bibbee (57) ABSTRACT

A method for improving the performance of recognition by increasing the rate of recognition include executing a specific application, acquiring a user image from a camera while the specific application is executed, collecting a candidate group of non-contact type recognition patterns for an execution screen of the specific application by recognizing at least one of a user's face, eye and hand from the user image, determining an effective value from the collected candidate group of non-contact type recognition patterns, and updating a predefined default value by applying the determined effective value to the predefined default value. An electronic device for improving the performance of recognition and other embodiments also are disclosed.

18 Claims, 5 Drawing Sheets

METHOD AND ELECTRONIC DEVICE FOR IMPROVING PERFORMANCE OF NON-CONTACT TYPE RECOGNITION FUNCTION

CROSS-REFERENCE TO RELATED APPLICATION(S) AND CLAIM OF PRIORITY

The present application is related to and claims the benefit under 35 U.S.C. § 119(a) of a Korean patent application No. 10-2013-0036365 filed on Apr. 3, 2013 in the Korean Intellectual Property Office, the entire disclosure of which is hereby incorporated by reference.

TECHNICAL FIELD

The present disclosure relates to technology for improving the recognition performance of an electronic device. More particularly, the present disclosure relates to a method for improving the performance of a non-contact type recognition function of an electronic device and to such an electronic device implementing the method.

BACKGROUND

With communication technologies advanced recently, a great variety of electronic devices such as a mobile phone, a smart phone, a tablet PC, and the like are increasingly popularized due to their high usability and good portability. Nowadays, many manufacturers of electronic devices have grown very attentive to recognition technology capable of using much more intuitively a function provided by electronic devices. Particularly, recognition technology of a non-contact type is widely used in various electronic devices.

Non-contact type recognition technology may include facial recognition, iris recognition, motion recognition, and the like. Normally this non-contact type recognition technology has a process of extracting or tracking information associated with user's behavior or action and a process of identifying a user input by comparing the extracted information with matched data. Unfortunately, non-contact type recognition technology may often have a difficulty in exactly extracting information associated with user's behavior or action, thus failing to obtain a reliable user input. Specifically, an electronic device having a recognition function may provide default data necessary for pattern recognition matching at the manufacture thereof. Such default values are, however, set on the basis of generalized information. This causes a failure to reflect characteristics of individual users and thus deteriorates the rate of recognition. For example, an eye pattern required for eye recognition is set to a normal size as a default value. However, in actual, users' eye sizes may be often greater or smaller than a normal size. Therefore, recognition functions provided by an electronic device fail to directly reflect characteristics of individual users, and this causes a poor rate of recognition.

SUMMARY

To address the above-discussed deficiencies, it is a primary object to provide a method and electronic device for improving the performance of recognition by increasing the rate of recognition with regard to specific recognition technology as the device is used.

Particularly, embodiments of this disclosure provide a method and electronic device for improving the performance of non-contact type recognition such as facial recognition, iris recognition, motion recognition, and speech recognition by updating default recognition criteria, predefined at the manufacture, so as to fit a current user.

An embodiment in this disclosure may provide a method for improving a non-contact type recognition function of an electronic device. This method comprises executing a specific application; acquiring a user image from a camera while the specific application is executed; collecting a candidate group of non-contact type recognition patterns for an execution screen of the specific application by recognizing at least one of a user's face, eye and hand from the user image; determining an effective value from the collected candidate group of non-contact type recognition patterns; and updating a predefined default value by applying the determined effective value to the predefined default value.

Another embodiment in this disclosure may provide an electronic device that comprises a display unit configured to display a screen associated with an operation of the electronic device; a camera configured to collect a user image; and a control unit configured to collect a candidate group of non-contact type recognition patterns for a specific application by recognizing at least one of a user's face, eye and hand from a user image acquired from the camera while the specific application is executed, to determine an effective value from the collected candidate group of non-contact type recognition patterns, and to update a predefined default value by applying the determined effective value to the predefined default value.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 7, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged electronic devices. The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the embodiments described herein may be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "an image" includes reference to one or more of such images.

Techniques disclosed herein may be applied to a variety of electronic devices, also referred to as user devices, user terminals, mobile devices, etc., including, but not limited to, a mobile phone, a smart phone, a notebook, a laptop computer, a tablet PC, a handheld PC, a digital broadcasting terminal, a personal digital assistant (PDA), a portable multimedia player (PMP), a navigation terminal, a media player, a mobile medical device, a digital camera, a portable game console, an electronic dictionary, an electronic scheduler, a wearable device, and any other equivalents.

An electronic device disclosed herein has a non-contact type recognition function and supports a control function based on non-contact type recognition. In this disclosure, a non-contact type recognition function may include, but not limited to, facial recognition, iris recognition, hand motion recognition, speech recognition, and the like. Although the following embodiment of this disclosure will be focused on facial recognition, especially, eye recognition, this is exemplary only and not to be considered as a limitation. Embodiments disclosed herein may be favorably applied to any other non-contact type recognition.

In short, when a user takes a specific action toward an electronic device, the electronic device detects information about the specific action through a non-contact type recognition function. Then, based on the detected information, the electronic device determines a user input pattern matched with a user's action, and performs a particular function defined by the determined user input pattern.

Figure 1:
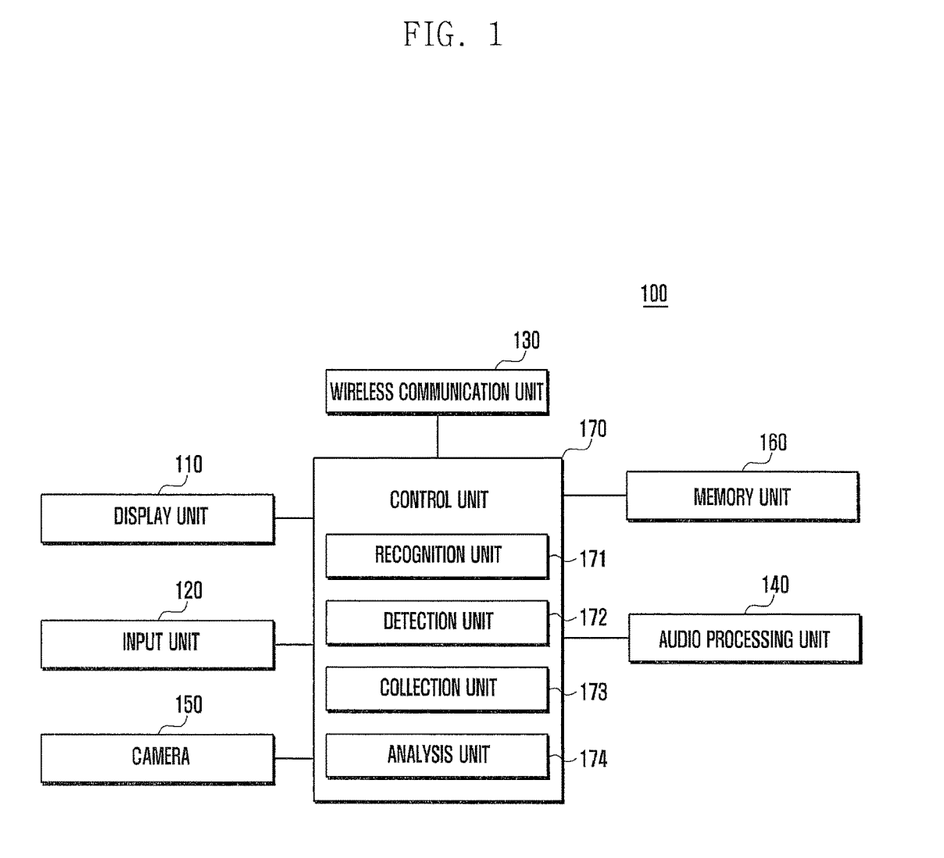
FIG. 1 is a block diagram illustrating an electronic device in accordance with an embodiment of the present disclosure.

FIG. 1 is a block diagram illustrating an electronic device in accordance with an embodiment of the present disclosure.

Referring to FIG. 1, the electronic device 100 may include a display unit 110, an input unit 120, a wireless communication unit 130, an audio processing unit 140, a camera 150, a memory unit 160, and a control unit 170.

The display unit 110 displays a variety of screens required for the operation of the electronic device 100. The display unit 110 receives image data from the control unit 170, converts the received data into analog signals, and displays the analog signals thereon. The display unit 110 may include a display panel configured to offer various screens associated with the operation of the electronic device 100, and a touch panel disposed on or under the display panel and configured to create a touch-based input event. The display unit 110 may provide a landscape display mode or a portrait display mode, depending on a rotation direction or a placed posture of the electronic device 100.

The input unit 120 creates a variety of input signals required for the operation of the electronic device 100. Namely, the input unit 120 creates a signal associated with a user setting or a function control of the electronic device 100, and transmits the created signal to the control unit 170. Then the control unit 170 controls a particular function in response to this input signal. Additionally, in case of including the touch panel, the display unit 110 may act as a part of the input unit 120. In this case, an input signal for the operation of the electronic device 100 may be created through the touch panel.

The wireless communication unit 130 performs a wireless communication of the electronic device 100. Namely, the wireless communication unit 130 performs a voice communication, a video communication, a data communication, etc. by establishing a suitable communication channel with any available communication network. Specifically, the wireless communication unit 130 may include a radio frequency (RF) transmitter that up-converts the frequency of an outgoing signal and amplifies the signal, an RF receiver that amplifies with low-noise an incoming signal and down-converts the frequency of the signal, and the like. In case the electronic device 100 fails to offer a wireless communication function, the wireless communication unit 130 may be omitted.

The audio processing unit 140 may include a speaker that outputs an audio signal created or decoded in the electronic device 100, and a microphone that collects an audio signal in order to support a voice call, a video call, a voice recording, or the like. The audio processing unit 140 may be formed of codec which may include a data codec for processing packet data and an audio codec for processing an audio signal such as voice.

The camera 150 captures or collects an image. The camera 150 may include a camera sensor that converts an entered optical signal into an electric signal, an image signal processor that converts an analog signal received from the camera sensor into digital data, a digital signal processor (DSP) that performs an image processing (e.g., scaling, noise removal, RGB conversion, etc.) for digital data received from the image signal processor in order to display it on the screen, and the like. The camera sensor may use, but not limited to, a charge-coupled device (CCD) sensor, a complementary metal-oxide semiconductor (CMOS) sensor, or the like. In some cases, the image signal processor may be replaced with or incorporated into the DSP.

The camera 150 collects a user image and transfers the collected image to the display unit 110 and the control unit 170. In case the electronic device 100 operates in a recognition function mode, the camera 150 may be turned on in the background under the control of the control unit 170 and then transfer a user image (e.g., face, hand, etc.) to the control unit 170 through any internal sensor. Although the camera 150 may be disposed respectively on both the front side and the rear side of a device body, the camera 150 turned on in a recognition function mode may be a front camera disposed on the front side.

The memory unit 160 stores an operating system (OS) of the electronic device 100, various applications, and various data created by or required for the operation of the electronic device 100. Such data may include all kinds of data produced by the execution of any application in the electronic device 100 or received from any external entity (e.g., an external server, other electronic device, etc.). The memory unit 160 may store a user interface provided in the electronic device 100 and various types of setting information associated with a function of the electronic device 100.

The control unit 170 controls the overall operation of the electronic device 100, controls a signal flow between internal components of the electronic device 100, and performs a function to process data. Further, the control unit 170 controls the supply of electric power from a battery to internal components. Once electric power is supplied, the control unit 170 controls a booting procedure and executes various application programs stored in a program region to perform a particular function of the electronic device 100. Particularly, the control unit 170 may control a non-contact type recognition function and related operations. For this, the control unit 170 may be composed of a recognition unit 171, a detection unit 172, a collection unit 173, and an analysis unit 174.

The recognition unit 171 supports a function to collect a user image from the camera 150, to recognize a user's face in the collected user image, and to track a user's eye region on the basis of the recognized user's face. Namely, the recognition unit 171 identifies the position of a user's eye region and extracts an eye pattern from the eye region. The recognition unit 171 may recognize the color of a face, the position of eyes and mouth, or the like, based on recognition technology such as facial recognition, iris recognition or iris scan, motion recognition or lariat feature tracking, thermal infrared recognition, or the like.

The detection unit 172 supports a function to detect a user input based on user's gaze by performing a pattern matching on the basis of the extracted eye pattern. For example, in case a user manipulates the electronic device 100, a user who gazes on the screen may stop gazing. In this case, the recognition unit 171 may extract a pattern of eyes by recognizing a user's eye. If a pattern matching shows that the extracted eye pattern corresponds to a pattern of non-gazing eyes, the detection unit 172 may determine that a user does not see the screen any more. Then the detection unit 172 may detect a user input that indicates the turn-off of the display unit 110.

Meanwhile, the electronic device 100 having an eye recognition function has a default value about an eye pattern which has been predefined for the recognition of a user's eye region at the manufacture of the device 100. For example, this default value may include information about the form of an eye region such as the contour, size, or color of the eye and pupil. Since this default value has been defined on the basis of a set model library at the manufacture of the device 100, the default value may fail to reflect information about eye features of individual users. Unfortunately, this may deteriorate the rate of eye recognition.

The collection unit 173 supports a function to collect information about a user's eye pattern. The collection unit 173 may repeatedly collect information about a user's eye pattern based on changes in a user's view or eye shape. Additionally, the collection unit 173 collects information about a user's eye pattern according to a predefined schedule. In this disclosure, a predefined schedule may mean any case in which a particular function is performed on the basis of eye recognition and/or any case in which a certain function requiring a change in a gazing position is performed. Such a schedule may define a time point and/or frequency for collecting information about a user's eye pattern. Also, the collection unit 173 may collect variations of a user's eye pattern caused by a predefined number of functions performed through a tutorial menu in a process of setting an eye recognition function.

The analysis unit 174 supports a function to analyze effective data on the basis of the collected eye patterns and to update a default value by means of the analyzed effective data. For example, if any case is determined as a wrong operation that happens in a process of collecting a candidate group of eye patterns, the analysis unit 174 may change any pattern determined as an ineffective candidate group to an effective candidate group. Additionally, in case user's eye patterns are collected more than a predefined frequency, the analysis unit 174 can classify effective candidate groups and determine an effective value by giving weight to concentrated eye pattern information.

Now, detailed operations of the electronic device will be described with reference to FIG. 2.

Figure 2:
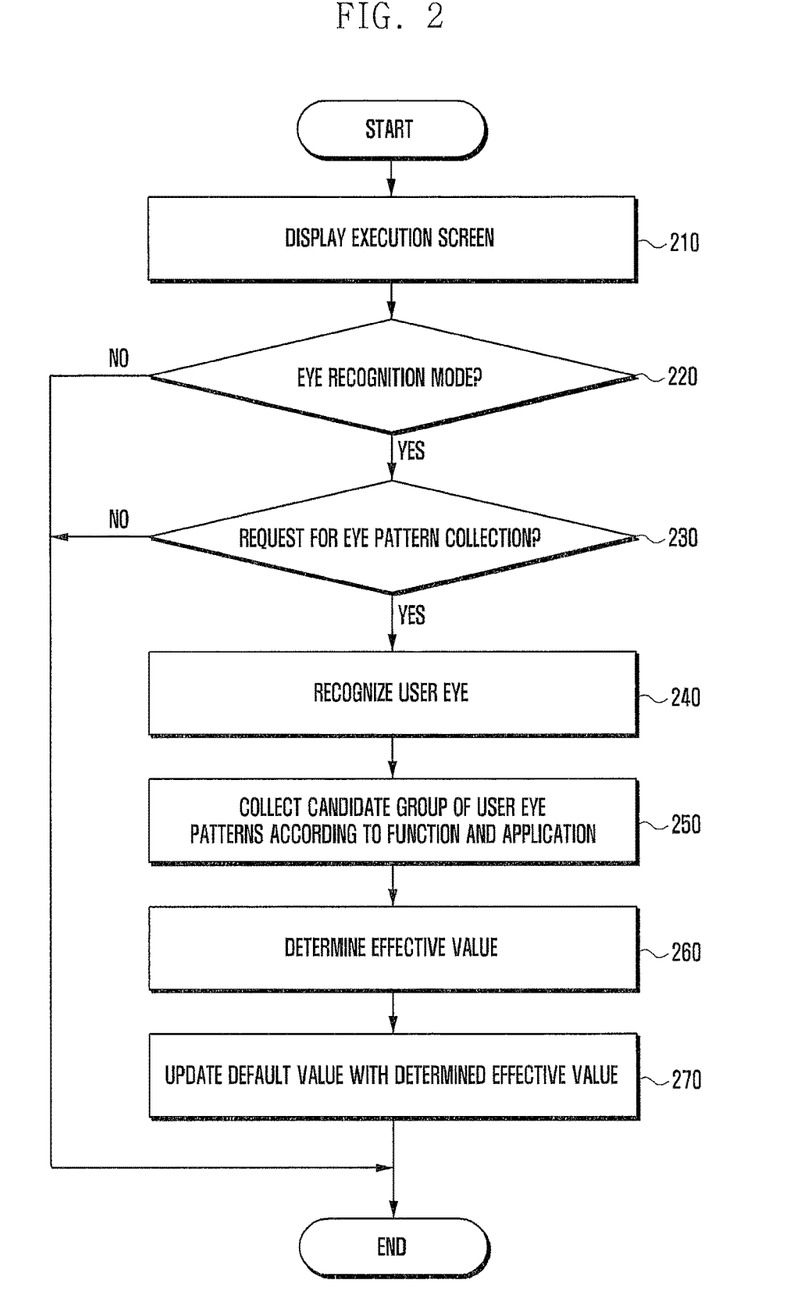
FIG. 2 is a flow diagram illustrating a method for improving recognition performance of an electronic device in accordance with an embodiment of the present disclosure.

FIG. 2 is a flow diagram illustrating a method for improving recognition performance of an electronic device in accordance with an embodiment of the present disclosure. In the present disclosure, the electronic device supports an eye recognition function to recognize a user's eye and then perform a corresponding function in response to an eye movement.

Referring to FIG. 2, at operation 210, the device 100 displays a specific execution screen on the display unit 110 at a user's request or according to a predefined schedule. A specific execution screen may include, but not limited to, a home screen, a function execution screen, an application execution screen, a menu screen, or the like.

At operation 220, the device 100 determines whether a current mode is an eye recognition mode. When there is a user's request or when a specific application supporting an eye recognition function is executed, an eye recognition mode may be activated. In this mode, the device 100 drives the camera 150 to recognize a user's eye. The camera 150 may be a front camera disposed on the front side of the device 100. The camera 150 collects a user image and transfers it to the control unit 170.

At operation 230, the device 100 determines whether a collection request signal for collecting a user's eye pattern is created in an eye recognition mode. Such a collection request signal may be created when a predefined schedule arrives. As mentioned above, a predefined schedule may mean any case in which a particular function is performed on the basis of eye recognition and/or any case in which a certain function requiring a change in a gazing position is performed, and further define a time point and/or frequency for collecting information about a user's eye pattern. For example, when a function to maintain a turn-on state of the display unit 110 is performed in response to user's gaze on the screen for a given time, when the display unit 110 changes a display mode of the screen according to a rotation direction or placed posture of the electronic device 100, or when a function to turn off the screen of the display unit 110 is performed in response to user's non-gaze on the screen, a collection request signal may be created.

When a request for collecting an eye pattern happens, the device 100 recognizes at operation 240 a user's eye on the basis of a user image acquired by the camera 150. For example, the device 100 recognizes a user's face in the acquired user image, identifies the position of a user's eye region in the recognized user's face, and extracts a pattern of a user's eye from the eye region. Here, an eye pattern may be data about an eye size, a pupil position, and a pupil direction.

In this disclosure, eye recognition may be classified into one case of recognizing a user's eye in response to a request for collecting an eye pattern and the other case of recognizing a user's eye in order to execute a particular function.

At operation 250, based on the extracted pattern of a user's eye, the device 100 collects a candidate group of user's eye patterns according to function and application. For example, when a user uses the device 100, a user's view or eye shape may be varied according to a specific application or specific function. The device 100 in this disclosure may repeatedly collect user's eye patterns caused by changes in such a user's view or eye shape. User's eye patterns may be collected according to a predefined schedule. Additionally, in a process of setting an eye recognition function, it is possible to collect variations of a user's eye pattern caused by a predefined number of functions performed through a tutorial menu. This function to collect user's eye patterns will be described with reference to FIGS. 3 and 4.

At operation 260, the device 100 determines an effective value of eye recognition pattern, based on the collected candidate group of eye patterns. At this operation, an effective value may vary according to function and application. For example, the device 100 classifies the collected candidate groups into eye pattern types such as an eye pattern of gazing on the screen, an eye pattern of not gazing on the screen, an eye pattern of gazing at the lower part of the screen, an eye pattern of gazing at the upper part of the screen, and the like. Based on a specific pattern, the device 100 may classify a matched pattern as effective data and the other pattern as ineffective data. For example, let's suppose that a case of not gazing on the screen corresponds to the 'A' pattern. Then, based on the 'A' pattern, the device 100 may classify specific patterns, which are considered to be not gazing on the screen among candidate groups, as effective data of the 'A' pattern, and classify the other patterns, which are considered to be gazing on the screen, as ineffective data of the 'A' pattern.

If any case is determined as a wrong operation that happens in a process of collecting a candidate group of eye patterns, the device 100 may invalidate any information determined as a specific pattern and then change it to an effective candidate group of other distinctive pattern.

For example, in case the device 100 turns off a display screen on the basis of determination that a user fails to gaze on the screen, the device 100 collects candidate groups according to a predefined schedule and classifies the collected candidate groups by their patterns. In this case, since a screen turn-off function is performed on the basis of determination that a user does not gaze on the screen, the collected eye patterns may be classified as being matched with the 'A' pattern. If any predefined condition (e.g., a case a user input is detected within N seconds) is satisfied after collection, the device 100 may invalidate any information classified as the 'A' pattern and classify again it as effective data of a screen gazing pattern. Meanwhile, in case user's eye patterns are collected more than a predefined frequency, the device 100 may classify effective candidate groups and determine an effective value by giving weight to concentrated eye pattern information.

After an effective value is determined on the basis of collected information about user's eye patterns, at operation 270 the device 100 updates a default value of an eye recognition pattern with the determined effective value. At this operation, an effective value may be any value to which an eye property of individual user who uses the device 100 is applied.

Figure 3:
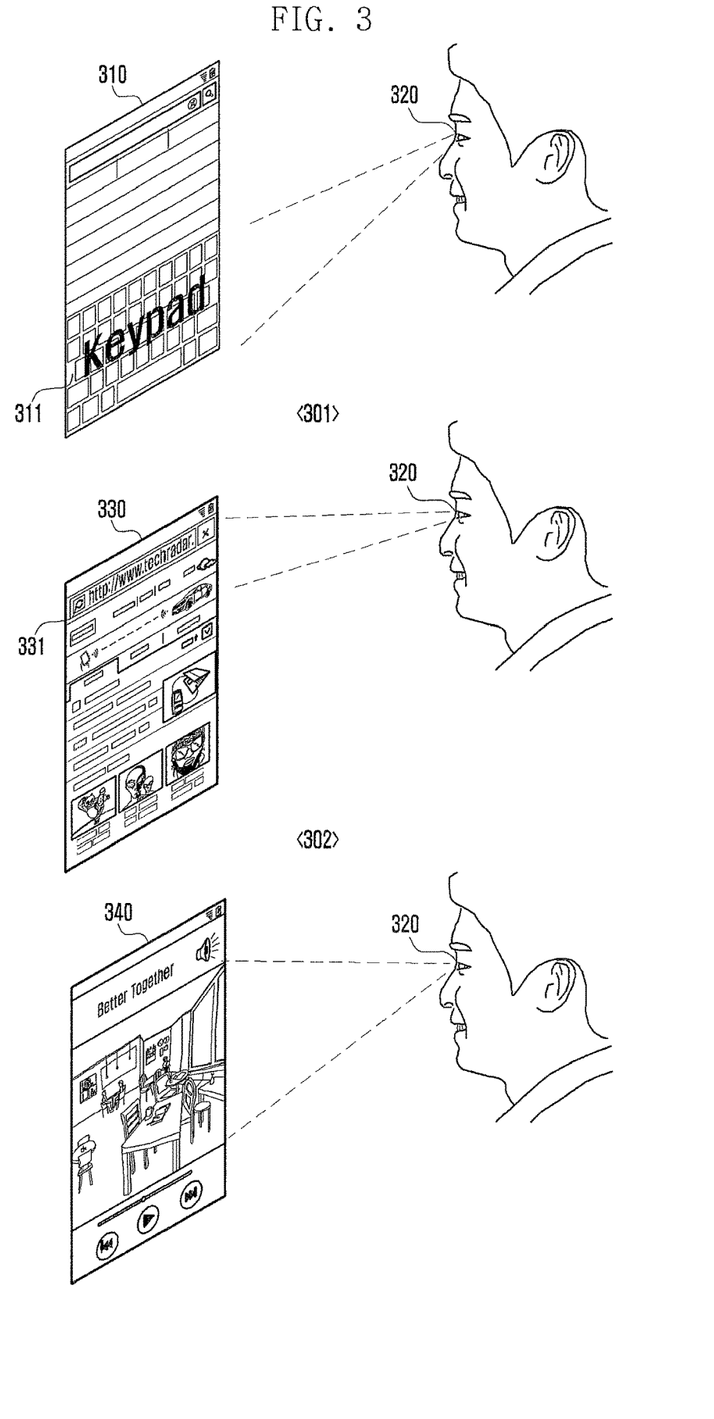
FIG. 3 is a schematic diagram illustrating a process of collecting a user's eye pattern in accordance with an embodiment of the present disclosure.

FIG. 3 is a schematic diagram illustrating a process of collecting a user's eye pattern in accordance with an embodiment of the present disclosure.

Referring to FIG. 3, the display unit 110 may display an execution screen of a particular application at a user's request or according to a predefined schedule. The electronic device 100 supports a function to collect a user's eye pattern which may be varied according to characteristics of the particular application.

For example, as shown in section 301 of FIG. 3, the display unit 110 may display a message creation screen 310 which may contain a recipient input window, a message input window, and a keypad 311. Normally the keypad 311 is disposed at a lower part of the display unit 110. In this case, a user 320 gazes at a lower part of the display unit 110 in order to enter characters through the keypad 311. Therefore, when a predefined schedule arrives, the device 100 collects a user's eye pattern of gazing at a lower part of the display unit 110.

In case a web screen 330 is displayed on the display unit 110 as shown in section 302 of FIG. 3, a user 320 may use an address window 331 disposed at an upper part of the web screen 330 in order to search for web sites. In this case, a user 320 gazes at an upper part of the display unit 110.

In case a video playback screen 340 is displayed on the display unit 110 as shown in section 303 of FIG. 3, a user 320 gazes at the entire screen or a central part of the display unit 110.

Like such cases, when a user manipulates the device 100, a user's view or eye shape may be varied according to application or function. Therefore, the device 100 collects information about a user's eye pattern, depending on a currently used application or function.

Additionally, the device 100 determines an effective value based on the collected eye pattern information and then updates a default eye pattern with an eye recognition pattern optimized to a specific application so as to improve an eye recognition function with regard to the specific application.

Figure 4:
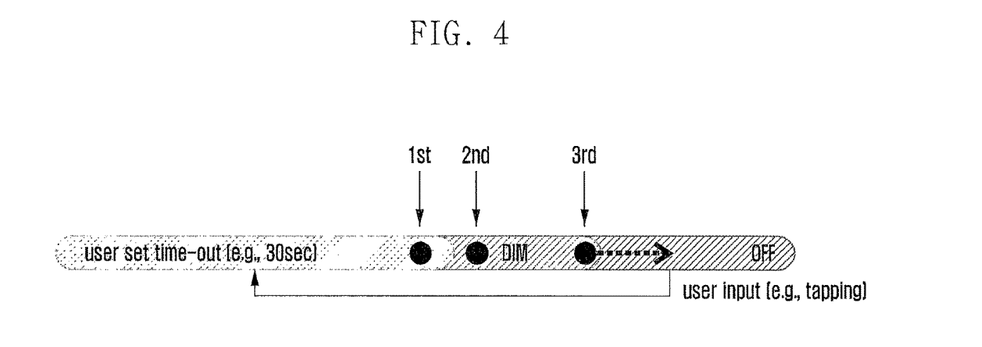
FIG. 4 is a schematic diagram illustrating a point of time to collect a user's eye pattern in accordance with an embodiment of the present disclosure.

FIG. 4 is a schematic diagram illustrating a point of time to collect a user's eye pattern in accordance with an embodiment of the present disclosure.

Referring to FIG. 4, the electronic device in this disclosure supports a function to repeatedly collect a user's eye pattern and to determine an effective candidate group of eye patterns from the collected patterns.

Although FIG. 4 shows a case in which a time point of collection is set based on a timeline, this is exemplary only and not to be considered as a limitation. Also, FIG. 4 shows a timeline for performing a function to turn off the display unit by determining that a user fails to gaze on the screen for a given time (e.g., 30 sec). In this case, the display unit may be in a turn-on state, a dim state, or a turn-off state. Here, a dim state is defined as a state in which the brightness of the screen is adjusted darkly for a given time before the display unit 110 is completely turned off.

In case a turn-off function is performed, the device 100 may collect information about a user's eye pattern by recognizing a user's eye just before entry into a dim state, after entry into a dim state, and just before entry into a turn-off state according to a predefined schedule. This is, however, exemplary only and not to be considered as a limitation. Alternatively, a user's eye pattern may be collected even after entry into a turn-off state. Like this, the frequency of collecting a user's eye pattern may be varied according to setting.

If a user's eye pattern collected three times for example is matched with a non-gazing pattern, the device determines such collected pattern as an effective candidate group of a non-gazing pattern.

By the way, even though a user gazes on the screen, the device may turn off the screen by recognizing a user's eye pattern as a non-gazing pattern. In this case, if any user input for turning on the screen is detected within N seconds for example, the device 100 may invalidate any candidate group classified as a non-gazing pattern and classify a user's eye pattern as a screen gazing pattern.

Figure 5:
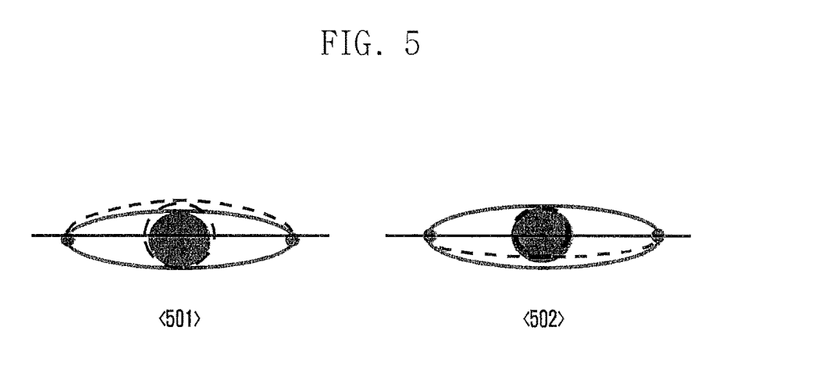
FIG. 5 is a schematic diagram illustrating effective data of a user's eye pattern in accordance with an embodiment of the present disclosure.

FIG. 5 is a schematic diagram illustrating effective data of a user's eye pattern in accordance with an embodiment of the present disclosure.

Referring to FIG. 5, the electronic device in this disclosure supports a function to classify candidate groups of user's eye patterns collected repeatedly, to determine an effective value, and to update a default value of an eye recognition pattern by applying the determined effective value.

For example, let's suppose that user's eye patterns are collected ten times for a specific application. For convenience and simplification, FIG. 5 employs a contour image. A reference number 510 indicates a default value which has been predefined for eye recognition at the manufacture of device.

While a specific application or function is executed, the device collects user's eye patterns. Collected patterns may be classified into nine times collected patterns 520 and only once collected pattern 530. In this case, by giving weight to the nine times collected patterns 520, the device 100 may determine the nine times collected patterns 520 as an effective candidate group and also determine the once collected pattern 530 as an ineffective candidate group.

Then the device 100 determines an effective value on the basis of an effective candidate group and updates the default value 510 with the determined effective value. Therefore, as shown in section 502 of FIG. 5, the device 100 may perform eye recognition on the basis of an updated and extended value 540 to which a user's eye property is applied. This may improve the rate of eye recognition.

Figure 6:
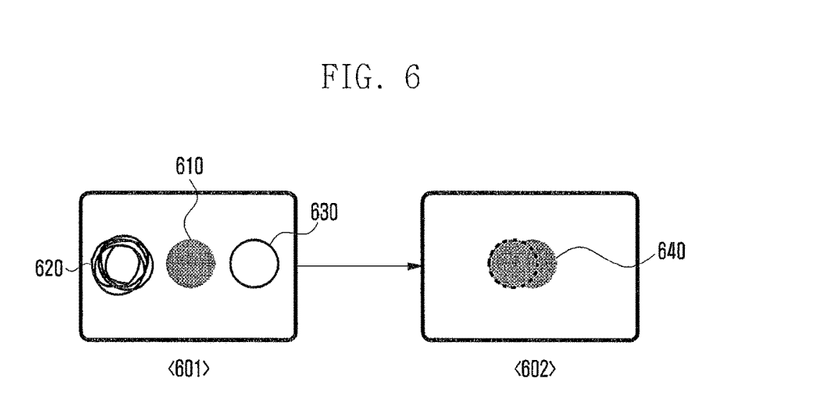
FIG. 6 is a schematic diagram illustrating an update result of a user's eye pattern in accordance with an embodiment of the present disclosure.

FIG. 6 is a schematic diagram illustrating an update result of a user's eye pattern in accordance with an embodiment of the present disclosure.

Referring to FIG. 6, an eye recognition pattern may be enlarged or reduced from a default pattern, depending on a user's eye property. For example, in case a user's eye size (or a pupil size, etc.) is greater than a default value as shown in section 601, the device sets an enlarged eye recognition pattern by applying a user's eye property to the default value. In case a user's eye size is smaller than a default value as shown in section 602, the device sets a reduced eye recognition pattern by applying a user's eye property to the default value.

Figure 7:
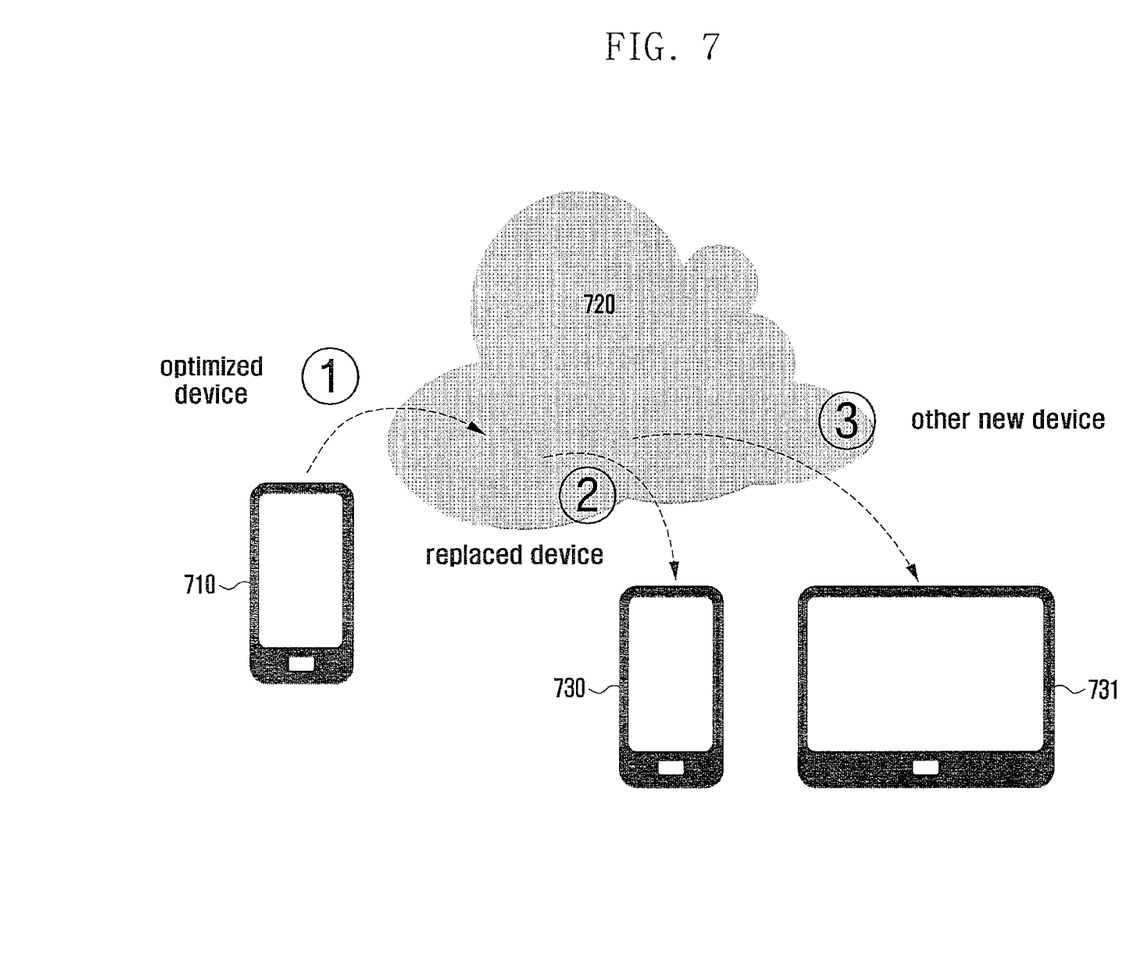
FIG. 7 is a schematic diagram illustrating a system for sharing a recognition function in accordance with an embodiment of the present disclosure.

FIG. 7 is a schematic diagram illustrating a system for sharing a recognition function in accordance with an embodiment of the present disclosure.

Referring to FIG. 7, disclosed techniques to improve the performance of a recognition function may be extended to a system, which may be composed of an electronic device 710 as discussed above in an embodiment, a cloud device 720, and other electronic devices 730 and 731. The cloud device 720 may include a wireless communication unit, a memory unit, and a control unit. Related descriptions will be omitted.

The electronic device 710 accesses the sharing system and supports a function to upload or download eye recognition information optimized to a user's eye property. Additionally, the device 710 supports a function to set a default value of an eye recognition pattern on the basis of optimized eye recognition information downloaded from the sharing system. Further, the device 710 may upload eye recognition information optimized to a user's eye property to the cloud device 720. In case a user changes his or her device or uses a new device, a user may download, from the cloud device 720 to the other devices 730 and 731, eye recognition information optimized to a user's eye properties. Then the other devices 730 and 731 set a default eye recognition pattern on the basis of the downloaded eye recognition information. Like this, since a user's eye property is applied even in a change of device, an eye recognition function may be improved.

Although the present disclosure has been described with an exemplary embodiment, various changes and modifications may be suggested to one skilled in the art. It is intended that the present disclosure encompass such changes and modifications as fall within the scope of the appended claims.

What is claimed is:
1. A method for improving a non-contact type recognition function of an electronic device, the method comprising:
    recognizing an eye pattern by acquiring a user image while an application program is being executed;
    collecting a plurality of candidate groups of non-contact type recognition patterns according to each of a plurality of application programs, wherein the plurality of candidate groups includes a plurality of images of eyes;
    determining each of a plurality of effective values from the collected plurality of candidate groups of non-contact type recognition patterns for each application program, wherein the effective values indicate a plurality of different staring directions and shapes of eyes for the plurality of application programs; and
    updating a predefined default value corresponding to each application program by applying each determined effective value to the predefined default value,
    wherein the determining of the each of the plurality of effective values comprises:
    performing a function corresponding to a specific pattern;
    identifying that the specific pattern causes a wrong operation if a user input for cancelling the function is detected within a predetermined time; and
    invalidating information determined as the specific pattern.

2. The method of claim 1, further comprising:
acquiring the user image according to a predefined time point and frequency in case a particular function of the application program is performed in accordance with a recognition pattern based on the predefined default value.

3. The method of claim 1, wherein collecting the plurality of candidate groups of non-contact type recognition patterns comprises collecting at least one of an eye recognition pattern, a hand motion pattern, or a face look pattern.

4. The method of claim 1, wherein collecting the plurality of candidate groups of non-contact type recognition patterns comprises:
collecting non-contact type recognition patterns caused by one or more functions performed through a tutorial menu.

5. The method of claim 1, wherein determining the plurality of effective values comprises:
determining the plurality of effective values with recognition patterns having weight among the non-contact type recognition patterns, in case the plurality of candidate groups are collected more than a predefined frequency.

6. The method of claim 1, further comprising:
classifying the plurality of candidate groups by types of the non-contact type recognition patterns, wherein if a user input opposite to a classifying result is detected after the collected plurality of candidate groups are classified as a first specific pattern, the plurality of candidate groups classified as the first specific pattern is invalidated and changed to effective data of a second specific pattern.

7. The method of claim 1, wherein one of the plurality of application programs is a virtual keypad displayed on a screen.

8. The method of claim 7, wherein the plurality of candidate groups of non-contact type recognition patterns comprises a gazing pattern on the virtual keypad.

9. The method of claim 1, further comprising:
uploading eye recognition information optimized to a user's eye properties to a cloud device.

10. An electronic device comprising:
a display configured to display a screen associated with an operation of the electronic device;
a camera configured to acquire a plurality of images of eyes; and
a controller configured to:
recognize an eye pattern by controlling the camera to acquire a user image while an application program is being executed;
collect a plurality of candidate groups of non-contact type recognition patterns according to each of a plurality of application programs, wherein the plurality of candidate groups includes a plurality of images of eyes;
determine each of a plurality of effective values from the collected plurality of candidate groups of non-contact type recognition patterns for each application program, wherein the effective values indicate a plurality of different staring directions and shapes of eyes for the plurality of application programs; and
update a predefined default value corresponding to each application program by applying each determined effective value to the predefined default value,
wherein the determining of the each of the plurality of effective values comprises:
performing a function corresponding to a specific pattern;
identifying that the specific pattern causes a wrong operation if a user input for cancelling the function is detected within a predetermined time; and
invalidating information determined as the specific pattern.

11. The electronic device of claim 10, wherein the controller is further configured to acquire the user image according to a predefined time point and frequency in case a particular function of each application program is performed in accordance with a recognition pattern based on the predefined default value.

12. The electronic device of claim 10, wherein the controller is further configured to collect at least one of an eye recognition pattern, a hand motion pattern, or a face look pattern.

13. The electronic device of claim 10, wherein the controller is further configured to collect the non-contact type recognition patterns caused by one or more functions performed through a tutorial menu.

14. The electronic device of claim 10, wherein the controller is further configured to determine the plurality of effective values with recognition patterns having weights among the non-contact type recognition patterns, in case each candidate group is collected more than a predefined frequency.

15. The electronic device of claim 10, wherein the controller is further configured to classify the plurality of candidate groups by types of the non-contact type recognition patterns, if a user input opposite to a classifying result is detected after the collected plurality of candidate groups are classified as a first specific pattern, to invalidate a candidate group classified as the first specific pattern, and to change to effective data of a second specific pattern.

16. The electronic device of claim 10, wherein the controller is further configured to upload or download the updated value to or from a sharing system that is configured to share with another device, and to set the default value with a value that is downloaded from the sharing system.

17. The electronic device of claim 10, wherein one of the plurality of application programs is a virtual keypad displayed on a screen.

18. The electronic device of claim 17, wherein the plurality of candidate groups of non-contact type recognition patterns comprises a gazing pattern on the virtual keypad.

* * * * *